United States Patent [19]

Eldridge

[11] Patent Number: 4,705,171
[45] Date of Patent: Nov. 10, 1987

[54] WRAPPER FOR DELIVERING STERILE DISPOSABLES

[75] Inventor: Charles J. Eldridge, Pennsauken, N.J.

[73] Assignee: Temple University-of the Commonwealth System of Higher Education, Philadelphia, Pa.

[21] Appl. No.: 932,859

[22] Filed: Nov. 20, 1986

[51] Int. Cl.[4] ............................................. A61B 19/00
[52] U.S. Cl. .................................... 206/438; 206/440; 206/494; 206/278; 229/87 A; 150/52 R; 128/132 D; 53/412; 53/461
[58] Field of Search ............... 206/278, 438, 440, 494, 206/828; 229/87 A, 87 S; 150/52 R, 52 B; 383/73; 128/132 D; 53/219, 412, 461

[56] References Cited

U.S. PATENT DOCUMENTS

| D. 239,566 | 4/1976 | Vogt .................................... D59/2 R |
| 2,269,915 | 1/1942 | Porter ................................ 229/87 A |
| 2,734,543 | 2/1956 | Hunter ............................... 150/52 R |
| 3,107,786 | 10/1963 | Adelman ............................ 206/63.2 |
| 3,225,920 | 12/1965 | Reilly ................................ 229/87 A |
| 3,359,569 | 12/1967 | Rotanz et al ................... 206/440 X |
| 3,366,228 | 1/1968 | Nye ....................................... 206/46 |
| 3,384,225 | 5/1968 | Nye ...................................... 206/63.2 |
| 3,889,667 | 6/1975 | Collins ........................... 128/132 D |
| 4,041,203 | 8/1977 | Brock et al. ......................... 428/157 |
| 4,099,614 | 7/1978 | Heissenberger ................ 206/438 X |
| 4,519,183 | 5/1985 | Parody ................................ 53/461 |

FOREIGN PATENT DOCUMENTS 738269  7/1966  Canada ................................ 206/278

Primary Examiner—Stephen Marcus
Assistant Examiner—Michael J. Shea
Attorney, Agent, or Firm—Seidel, Gonda, Goldhammer & Abbott

[57] ABSTRACT

The present invention is directed to an improved package for wrapping sterile disposable articles, such as surgical gowns. The package generally includes a generally rectangular wrapping material having corners. A strap is generally T-shaped and has three free ends. Each free end of the strap is affixed adjacent one corner of the material. A pull tab is affixed to the strap. The package is opened by pulling the tab away from the package. The sterile article is wrapped by folding the corners of the material over the article and tucking one corner under the other corners.

6 Claims, 11 Drawing Figures

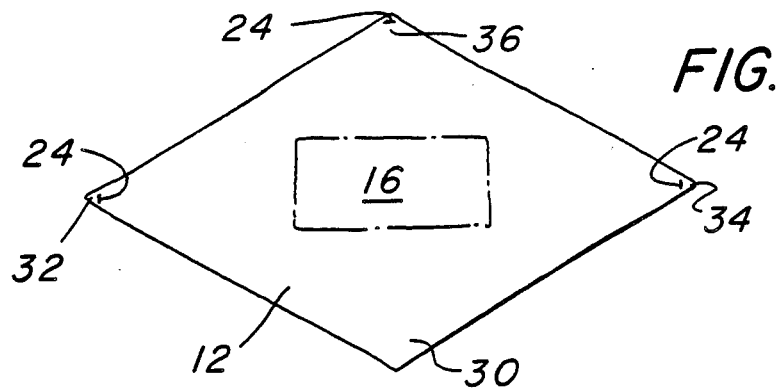
FIG. 4
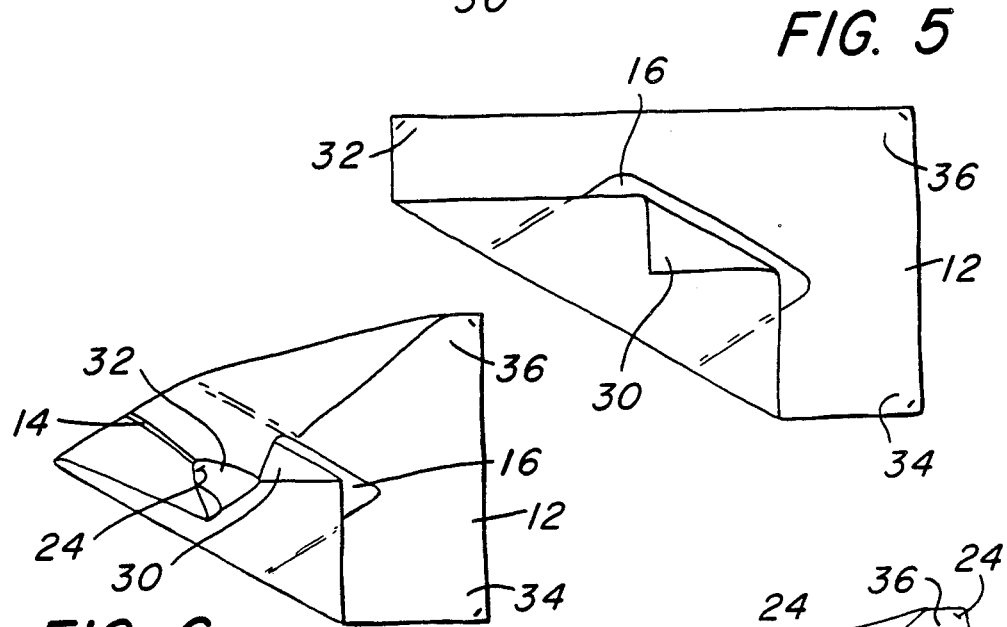
FIG. 5
FIG. 6
FIG. 7
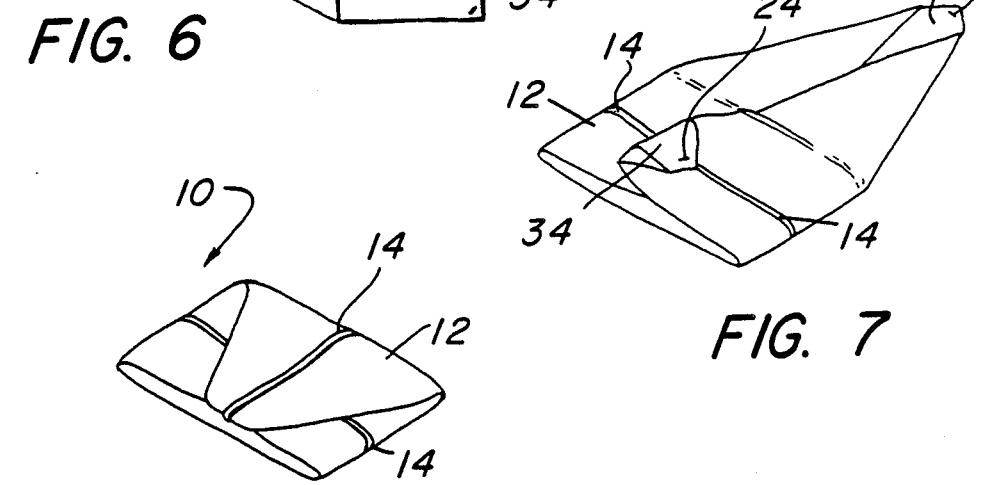
FIG. 8

WRAPPER FOR DELIVERING STERILE DISPOSABLES

SCOPE OF THE INVENTION

The present invention is directed to an improved package for wrapping sterile disposables.

BACKGROUND OF THE INVENTION

Heretofore, sterile disposable surgical garments have been wrapped in a sterile material. While removing the material surrounding the garment, the "sterile field" protecting the garment can be destroyed by the insertion of the unwrapper's (i.e., nurse) hands. Contamination of the "sterile field" increases the risk of transferring contaminants to the sterile garment and ultimately to the sterile field created around the patient. Accordingly, many doctors and hospitals prefer that the contaminated gown be discarded.

Additionally, to unwrap the sterile garment required numerous motions by the nurse. Such wasted motion is time consuming, especially before complicated procedures which may require as many as fifty or more sterile items.

U.S. Pat. No. 3,107,786 is directed to a package for surgical gloves. The package comprises a rectangular inner panel and a square outer panel. The inner panel is folded over onto itself and holds the gloves. The outer panel is then folded over the inner panel to form an envelope. Tape is used to fix the outer package in place.

U.S. Pat. No. 3,366,228 is directed to a surgical glove package. The package comprises an inner wrapping which is generally rectangular in shape. The inner wrapping is folded over onto itself to contain gloves. The inner wrap is enclosed within a rectangular outer wrap. The outer wrap is sealed with tape.

U.S. Pat. No. 3,384,225 is a sterile package for gloves which comprises an inner rectangular wrapper in which gloves are contained and an outer wrapper which is generally rectangular and folded over the inner wrapper.

The Kimberly-Clark Corporation surgical gown No. 9011 is a surgical gown upon which the present invention is based. The wrapping material used to surround this gown is exemplary of sterile wrapping material. See U.S. Pat. No. 4,041,203 and U.S. Pat. No. Des. 239,566. But, the wrapper includes no pull tab or strap, which will be described in greater detail below. The Kimberly-Clark wrapper requires at least three separate movements to open. Each movement is associated with unfolding a corner of the wrap away from the sterile garment contained within.

SUMMARY OF THE INVENTION

The present invention is directed to a package for wrapping sterile articles and methods for wrapping and unwrapping the sterile article.

The package for wrapping a sterile article includes a generally rectangular wrapping material having corner portions. A strap means is generally T-shaped and has three free ends. Each free end of said strap means is affixed adjacent one said corner portion. A pull means is affixed to the strap means.

The methods for wrapping and unwrapping a sterile article begin with providing the package described above.

The method of unwrapping the sterile article further comprises the steps of grasping the package along an edge portion thereof, with the pull means oriented downwardly. The pull means is grasped and pulled downwardly. The package is then removed from around the sterile article.

The method for wrapping the sterile article further comprises the steps of placing the sterile article on a side of the material opposite the strap means. The article is generally placed at the center portion of the material. The lower corner portion of the package is folded over the article. The lateral corner portions of the package are then sequentially folded over the lower corner portion. And finally, the top corner portion is folded over the lateral corner portions of the package and tucked below the lateral corner portions.

DESCRIPTION OF THE DRAWINGS

For the purpose of illustrating the invention, there is shown in the drawings a form which is presently preferred; it being understood, however, that this invention is not limited to the precise arrangements and instrumentalities shown.

FIGS. 4–8 sequentially illustrate the preferred method of wrapping a sterile article.

DESCRIPTION OF THE INVENTION

Figure 1:
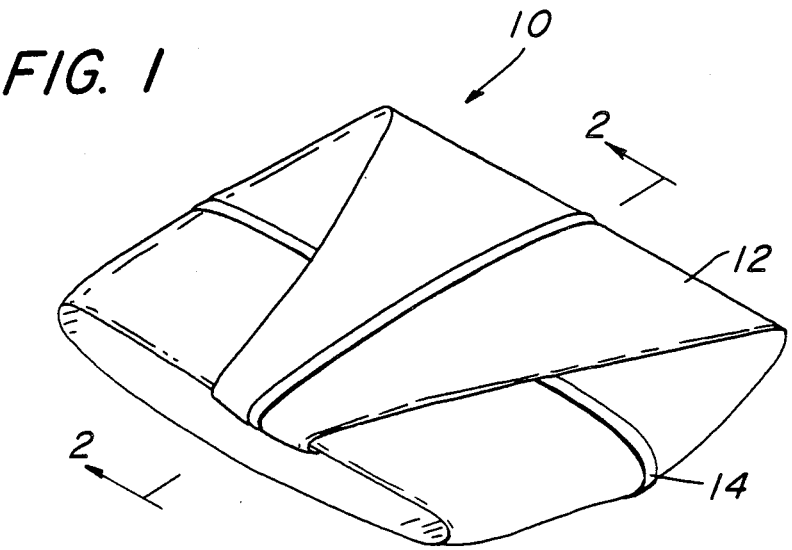
FIG. 1 is an isometric view of a preferred embodiment of the present invention.
Figure 2:
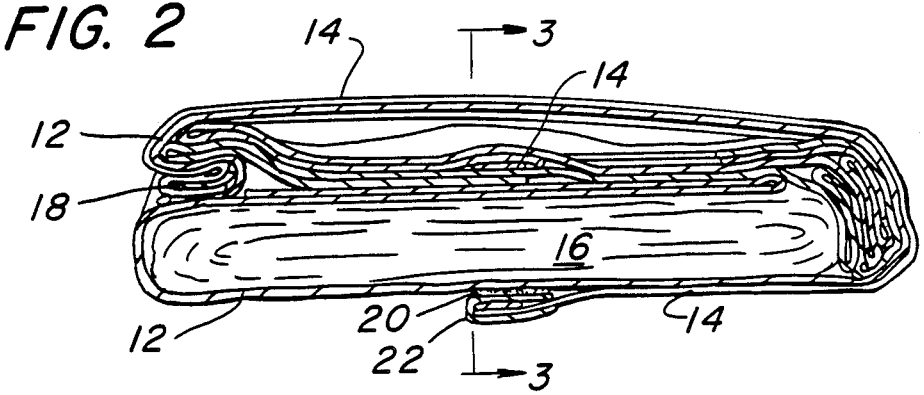
FIG. 2 is a sectional view of the present invention taken generally along line 2—2 of FIG. 1.
Figure 3:
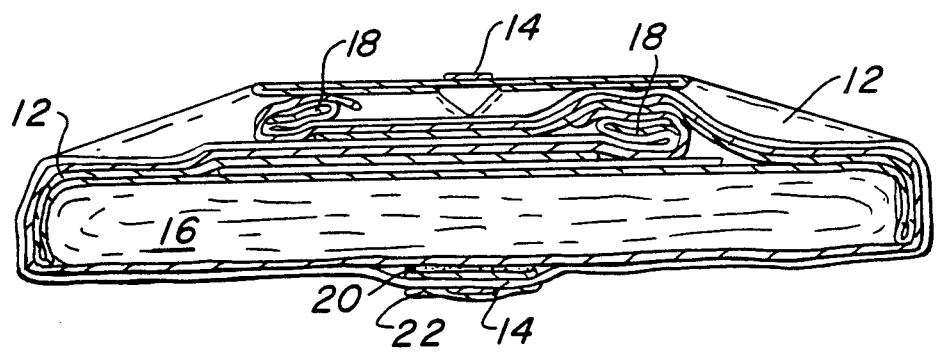
FIG. 3 is a sectional view of the present invention taken generally along line 3—3 of FIG. 2.

Referring to the drawings wherein like numerals indicated like elements, there is shown in FIG. 1 an illustration of the preferred embodiment of the present invention generally denoted 10. A sterile article or garment 16 is located within package 10. See FIGS. 2 and 3. The garment 16 can be a surgical gown.

The sterile package 10 generally comprises a wrapping material 12 having a strap 14 affixed thereto. U.S. Pat. No. 4,041,203 and U.S. Pat. No. Des. 239,566 are incorporated herein by reference. These two patents describe a preferred wrapping material 12. Strap 14 is generally T-shaped (see FIG. 9). The T-shaped strap 14 has three free ends. The vertex of the T-shaped strap 14 is generally located in the central portion of material 12. The free ends preferably must extend to the edges of material 12 in the corner portions. See FIGS. 10 and 11. Each free end of strap 14 is affixed to a corner portion of wrapping material 12 in any conventional manner, preferably by staples 24 (see FIG. 4).

Preferably at each point of attachment, a re-enforcing member 18 is also attached. The re-enforcement member 18 is located and affixed between the free end and the material 12. Re-enforcing member 18 is to prevent straps 14 from becoming detached from material 12.

At the vertex of the T-shaped strap 14, there is preferably included a tab 22. Tab 22 may take the form of a rectangular piece of material which is folded over the vertex of the T-shaped strap 14. Tab 22 is where the user should pull the strap 14.

The material of construction for the strap 14 and tab 22 are well known to those skilled in the art.

An adhesive material 20 is placed on an external surface of tab 22 which faces material 12. The adhesive material 20 is to temporarily affix tab 22 and strap 14 to material 12. Adhesive 20 is any adhesive which is well known to those skilled in the art and which does not permanently adhere tab 22 to material 12.

In FIGS. 4-8, the preferred method of wrapping the article 16 is illustrated. Referring to FIG. 4, wrapping material 12 is opened and placed on any flat surface with the attached strap 14 facing downwardly. The bottom corner portion 30 has no free end of strap 14 affixed thereto. The terms bottom, top, right hand and left hand are merely illustrative and are not limiting.

The article 16 is placed on material 12. Article 16 is generally placed in a central portion of material 12. Bottom corner portion 30 is folded over article 16 and the corner portion 30 is folded back onto itself (see FIG. 5).

A left hand corner portion 32 is folded over the folded bottom corner portion 30 and then back onto itself (see FIG. 6).

A right hand corner portion 34 is then folded over the left hand corner portion 32 and the right corner portion is folded back onto itself (see FIG. 7). Of course, it is understood that the order of folding the right hand and left hand corner portions is reversible.

A top corner portion 36 is folded over the right and left corner portions 32 and 34. The top corner portion 36 is then tucked below left and right corner portions 32 and 34 (see FIG. 8).

Figure 9:
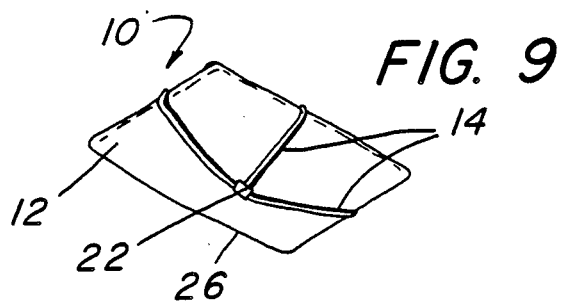
FIGS. 9–11 sequentially illustrate the preferred method of unwrapping the sterile article.
Figure 10:
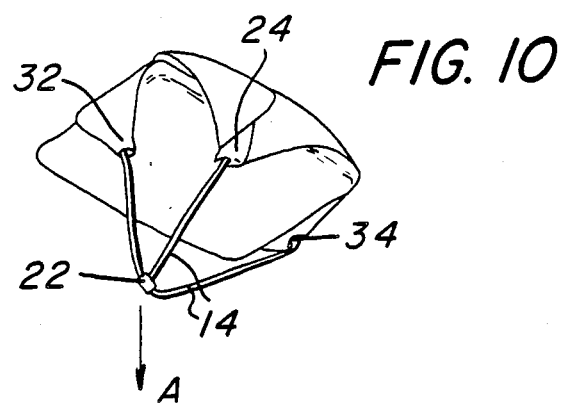
Figure 11:
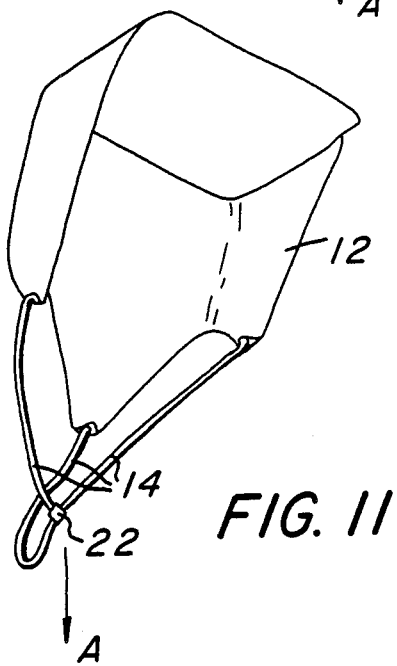

The method of unwrapping package 10 is illustrated in FIGS. 9-11. Package 10 is grasped along an edge portion 26. Edge portion 26 corresponds to the side of package 10 formed by bottom corner portion 30. The thumb of the unwrapper (nurse) is generally placed under tucked corner portion 36. The nurse grasps pull tab 22 with his or her free hand. While holding package 10 firmly, tab 22 is pulled downwardly in the direction of arrow A. See FIG. 10. The right, left, and top corner portions of material 12 are pulled from their wrapped positions and the package 10 is opened. The garment 16 is unwrapped and no hand has been inserted or yet touched the garment 16.

The present invention may be embodied in other specific forms without departing from the spirit or essential attributes thereof and, accordingly, references should be made to the appended claims, rather than to the foregoing specification, as indicating the scope of the invention.

I claim:

1. A package for wrapping a sterile article comprises:
   a generally rectangular wrapping material having corner portions;
   a strap means being generally T-shaped and having three free ends;
   each free end of said strap means being affixed adjacent one said corner portion; and
   a pull means being affixed to said strap means.

2. The package according to claim 1 further comprising:
   a re-enforcement member affixed at each attachment between said free end and said corner portion.

3. The package according to claim 1 further comprising:
   an adhesive material which is located on an external surface of said pull means which faces said material.

4. A package for wrapping a sterile article comprises:
   a generally rectangular wrapping material having corner portions;
   a strap means being generally T-shaped and having three free ends,
   each free end of said strap means being affixed adjacent one said corner portion;
   a re-enforcement member being affixed at each attachment between said free end and said corner portion; and a pull means being affixed to said strap means;
   an adhesive material, which is located on an external surface of said pull means which faces said material.

5. A method for unwrapping a sterile article comprising the steps of:
   providing a package containing the sterile article, said package includes a generally rectangular wrapping material having corner portions, a strap means being generally T-shaped and having three free ends, each free end of said strap means being affixed adjacent one said corner portion, and a pull means being affixed to said strap means;
   grasping said package along an edge thereof with said pull means oriented downwardly;
   grasping said pull means;
   pulling said pull means away from said package;
   whereby said package is removed from the sterile article.

6. A method for wrapping a sterile article comprising the steps of:
   providing a package for wrapping the sterile article, said package includes a generally rectangular wrapping material having corner portions, a strap means being generally T-shaped and having three free ends, each free end of said strap means being affixed adjacent one said corner portion, and a pull means being affixed to said strap means;
   placing the sterile article on a side of said material opposite said strap means, the article being generally placed at the central portion of the material;
   folding a lower corner portion of said package over said article;
   sequentially folding lateral corner portions of said package over said lower corner portion;
   folding a top corner portion over said lateral portions and tucking said top corner portion below said lateral corner portions.

* * * * *